US00PP10921P

United States Patent [19]

Van Der Voort

[11] Patent Number: Plant 10,921

[45] Date of Patent: May 25, 1999

[54] SPATHIPHYLLUM PLANT NAMED 'VIVALDI'

[75] Inventor: Chris Van Der Voort, LA Honselersdijk, Netherlands

[73] Assignee: Agriom B.V., Aalsmeer, Netherlands

[21] Appl. No.: 09/004,126

[22] Filed: Jan. 7, 1998

[51] Int. Cl.[6] ..... A01H 5/00

[52] U.S. Cl. ..... Plt./364

[58] Field of Search ..... Plt./364

[56] References Cited

U.S. PATENT DOCUMENTS

P.P. 8,844 7/1994 Van Dordrecht ..... Plt./364

*Primary Examiner*—Howard J. Locker

*Assistant Examiner*—Kent L. Bell

*Attorney, Agent, or Firm*—C. A. Whealy

[57] ABSTRACT

A distinct cultivar of Spathiphyllum plant named 'Vivaldi', characterized by its upright and outwardly arching plant habit; moderate vigor; dark green leaves that are held horizontal to the petiole; early flowering; numerous white spathes that are positioned about 10 cm above the foliage on strong and erect peduncles; spadices that do not produce pollen; and long-lasting inflorescences.

1 Drawing Sheet

The present invention relates to a new and distinct cultivar of Spathiphyllum plant, botanically known as Spathiphyllum, and hereinafter referred to by the cultivar name 'Vivaldi'.

The new cultivar is a product of a planned and controlled breeding program conducted by the inventor in Honselersdijk, The Netherlands. The objective of the breeding program is to create new Spathiphyllum cultivars with desirable plant shape and without pollen formation. The new cultivar originated from a deliberate cross by the inventor between two unidentified proprietary Spathiphyllum selections. The cultivar 'Vivaldi' was discovered and selected by the inventor as a plant within the progeny of the stated cross in a controlled environment in Honselersdijk, The Netherlands, in 1993.

Asexual propagation of the new cultivar by division and/or tissue culture at Honselersdijk,The Netherlands, has shown that the unique features of this new Spathiphyllum plant are stable and reproduced true to type in successive generations of asexual propagation.

The new Spathiphyllum has not been observed under all possible environmental conditions. The phenotype may vary somewhat with variations in environment such as temperature and light intensity, without, however, any variance in genotype. The following observations, measurements and comparisons describe plants grown in Honselerdijk, The Netherlands, under commercial greenhouse conditions.

The following traits have been repeatedly observed and are determined to be the unique characteristics of 'Vivaldi'. These characteristics in combination distinguish 'Vivaldi' as a new and distinct cultivar:

1. Upright and outwardly arching plant habit.
2. Moderate vigor.
3. Dark green leaves that are held horizontal to the petiole.
4. Early flowering.
5. Numerous white spathes that are positioned about 10 cm above the foliage on strong and erect peduncles.
6. Spadices that do not produce pollen.
7. Long-lasting inflorescences.

The new Spathiphyllum can be compared to the commercial cultivar 'Ceres' (disclosed in U.S. Plant Pat. No. 8,844). However in side-by-side comparisons conducted in Honselersdijk, The Netherlands, plants of the new Spathiphyllum differed from plants of the cultivar 'Ceres' in the following characteristics:

1. Plants of the new Spathiphyllum are smaller than plants of the cultivar 'Ceres'.
2. Leaves of plants of the new Spathiphyllum are slightly darker in color than leaves of plants of the cultivar 'Ceres'.
3. Plants of the new Spathiphyllum have larger spathes and spadices than plants of the cultivar 'Ceres'.
4. Spadices of plants of the new Spathiphyllum do not produce pollen whereas spadices of plants of the cultivar 'Ceres' produce a significant amount of pollen.
5. Seed formation has not been observed on plants of the new Spathiphyllum, however seed formation has been observed on plants of the cultivar 'Ceres'.

BRIEF DESCRIPTION OF THE PHOTOGRAPHS

The accompanying colored photographs illustrate the overall appearance of the new cultivar, showing the colors as true as it is reasonably possible to obtain in colored reproductions of this type.

The photograph at the top of the sheet comprises a side perspective view of a typical potted plant of 'Vivaldi'.

The photograph at the bottom of the sheet comprises a close-up view of a typical inflorescence of 'Vivaldi'. Inflorescence and foliage colors in the photographs may appear different than the actual colors due to light reflectance.

DETAILED BOTANICAL DESCRIPTION

The following observations and measurements describe plants grown in Honselersdijk, The Netherlands, in a glass-covered greenhouse with day and night temperatures ranging from 18 to 22° C. In the following description, color references are made to The Royal Horticultural Society Colour Chart except where general terms of ordinary dictionary significance are used.

Botanical classification: Spathiphyllum cultivar 'Vivaldi'.

Parentage:

*Female parent.*—Unidentified proprietary Spathiphyllum selection.

*Male parent.*—Unidentified proprietary Spathiphyllum selection.

Propagation: By division or by tissue culture.

*Time to initiate roots.*—Summer: About 10 days at 22° C. Winter: About 14 days at 22° C.

*Time to develop roots.*—Summer: About 14 days at 22° C. Winter: About 18 days at 22° C.

*Rooting habit.*—Freely branching, numerous thick fleshy roots.

Plant description:

*Plant shape.*—Upright, outwardly arching, inverted triangle, symmetrical.

*Growth habit.*—Erect when young, becoming more outwardly arching as leaves develop. Numerous side shoots give plants a full, dense appearance. Appropriate for 20 to 25-cm containers.

*Plant height.*—About 80 cm from soil level to top of leaf plane.

*Plant diameter.*—About 60 cm.

*Plant vigor.*—Moderate vigor.

*Foliage description.*—Shape: Ovate. Length: About 25 cm. Width: About 10 cm. Margin: Entire. Surface: Incurved. Apex: Cuspidate. Base: Obtuse. Aspect: Mature leaves held perpendicular to petiole, with further development, leaves may begin to droop. Texture: Leathery, smooth, glabrous, durable. Color: Young, top side: 143A. Young, under side: 138B. Mature, top side: 137A. Mature, under side: 137C. Venation, top side: 137A. Venation, under side: 143C. Petiole length, primary shoots: About 35 cm. Petiole diameter, primary shoots, just above geniculum: About 6 mm. Petiole diameter, primary shoots, just below geniculum: About 5 mm. Geniculum diameter, primary shoots: About 7 mm. Length of petiole wing, primary shoots: About 24 cm. Width of petiole wing, primary shoots: About 5 mm. Petiole color: Young: 143C. Fully developed: Winged area: 137C. Above winged area: 143C. Geniculum: 143C.

Inflorescence description:

*Inflorescence arrangement.*—Concave spathe with spadix held about 10 cm above the foliage. Numerous inflorescences arise from leaf axils.

*Spathe longevity.*—Spathes are long-lasting, about 4 weeks.

*Spathe.*—Shape: Ovate. Length: About 18 cm. Width: About 10 cm. Aspect: Concave, curving over the spadix. Color: Before unrolling: White, 155B. Open spathe: Front: White, 155C. Back, White, 155C.

*Spadix.*—Length: About 6 cm. Diameter: About 1.5 cm. Color: Immature: 155B. Mature: 155D. Pollen: None observed.

*Peduncle.*—Aspect: Strong and erect. Length: About 70 cm. Diameter: About 6 mm. Color: Immature: 143C. Mature: 143A.

Disease resistance: No known Spathiphyllum diseases observed to date on plants grown under commercial greenhouse conditions.

Seed development: Seed development has not been observed.

It is claimed:

1. A new and distinct cultivar of Spathiphyllum plant named 'Vivaldi', as illustrated and described.

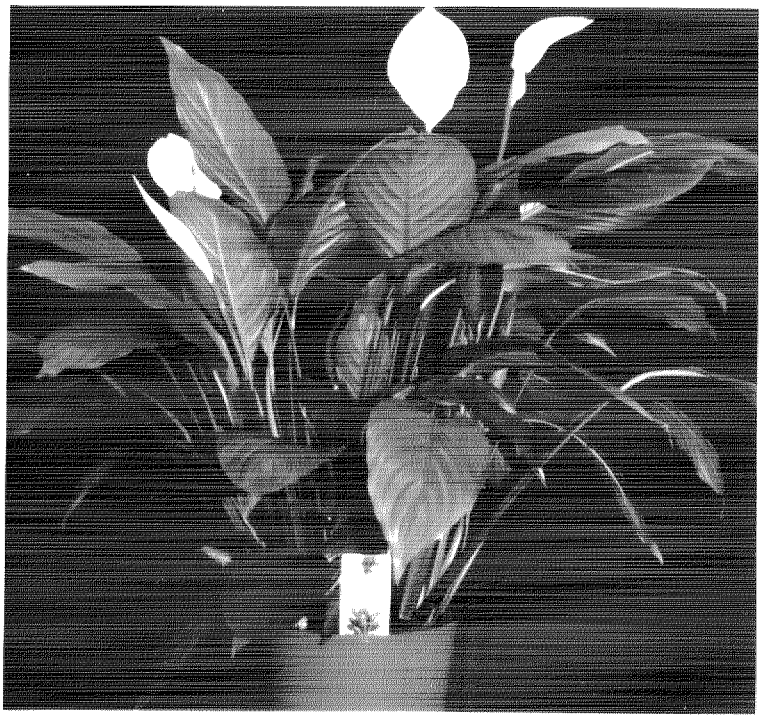
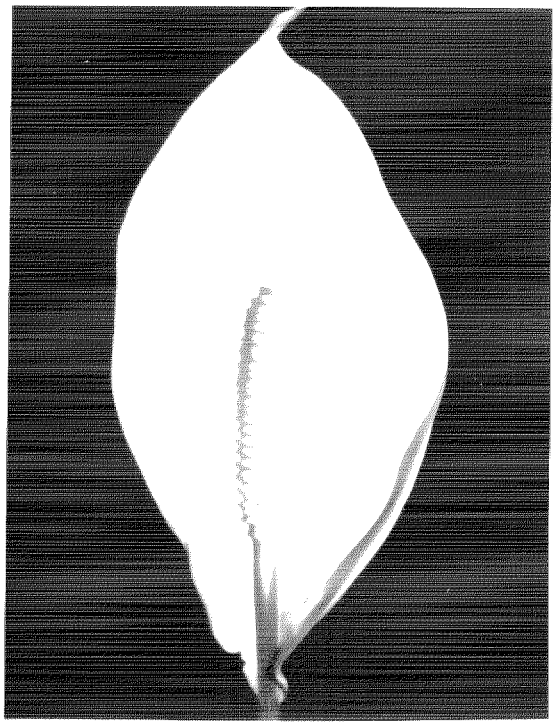

* * * * *